United States Patent
Ries et al.

[11] Patent Number: 5,824,105
[45] Date of Patent: *Oct. 20, 1998

[54] ASYMMETRIC FEMORAL PROSTHESIS

[75] Inventors: Michael Ries, Cooperstown, N.Y.; Brian Schumacher, Cordova, Tenn.

[73] Assignee: Smith & Nephew, Inc., Memphis, Tenn.

[ * ] Notice: The term of this patent shall not extend beyond the expiration date of Pat. No. 5,549,688.

[21] Appl. No.: 793,027

[22] PCT Filed: Aug. 1, 1995

[86] PCT No.: PCT/US95/09705

§ 371 Date: May 1, 1997

§ 102(e) Date: May 1, 1997

[87] PCT Pub. No.: WO96/03939

PCT Pub. Date: Feb. 15, 1996

Related U.S. Application Data

[63] Continuation-in-part of Ser. No. 285,917, Aug. 4, 1994, Pat. No. 5,549,688.

[51] Int. Cl.⁶ .................................................... A61F 2/38
[52] U.S. Cl. ................................................................ 623/20
[58] Field of Search .................................. 623/16, 18, 20

[56] References Cited

U.S. PATENT DOCUMENTS

| | | | |
|---|---|---|---|
| 4,081,866 | 4/1978 | Upshaw | 623/20 |
| 4,865,606 | 9/1989 | Rehder | 623/20 |
| 5,047,057 | 9/1991 | Lawes | 623/20 |
| 5,133,758 | 7/1992 | Hollister | 623/20 |
| 5,133,759 | 7/1992 | Turner | 623/20 |
| 5,192,328 | 3/1993 | Winters | 623/20 |
| 5,203,807 | 4/1993 | Evans et al. | 623/20 |
| 5,282,870 | 2/1994 | Moser et al. | 623/20 |
| 5,314,483 | 5/1994 | Wehrli et al. | 623/20 |
| 5,326,361 | 7/1994 | Hollister | 623/20 |

FOREIGN PATENT DOCUMENTS

| | | | |
|---|---|---|---|
| 719625 | 3/1980 | U.S.S.R. | 623/20 |
| 8603117 | 6/1986 | WIPO | 623/20 |

OTHER PUBLICATIONS

"Femoral Implant" (single sheet).

"The Technique of Total Knee Arthroplasty–Intraoperative Alignment and Instrumentation", pp. 130–133.

"Genesis Total Knee System", Smith & Nephew Richards Publication on Surgical Technique.

*Primary Examiner*—Mary Beth Jones
*Attorney, Agent, or Firm*—Pravel, Hewitt & Kimball

[57] ABSTRACT

A knee prosthesis includes a femoral prosthesis member having anterior, distal, and posterior articulating surface portions. The posterior articulating surface portions comprising a pair of condylar surface portions that are positioned at differing distances from the anterior non-articulating surface plane. The posterolateral articulating surface is a greater distance away from the anterior non-articulating surface than the posteromedial articulating surface. The femoral prosthesis has a non-articulating surface that includes a plurality of intersecting surfaces including at least distal, anterior, and posterior surfaces for receiving the patient's distal femur after it has been surgically prepared. A patella component having an articulating surface which articulates with the anterior articulating surface of the femoral component cooperates with a patella groove in the femoral component. The groove has a longitudinal axis which is located laterally with respect to the centerline of the superior region of the anterior articulating surface of the femoral component and which curves in a medial direction in the distal region of the anterior articulating surface of the femoral component. The angle of femoral rotation generally about the mechanical axis generally changes when going through a normal range of motion of the patient's knee while maintaining alignment of the femoral and tibial articular surfaces.

40 Claims, 7 Drawing Sheets

ASYMMETRIC FEMORAL PROSTHESIS

This is a continuation-in-part of application Ser. No. 08/285,917 filed Aug. 4, 1994, now U.S. Pat. No. 5,549,688.

The present invention relates to a medical prosthetic device and more particularly to an orthopedic medical prosthetic device. Even more particularly, the present invention relates to an improved asymmetric knee prosthesis and method of surgically implanting same wherein the prosthetic medial femoral condyles include a thinner medial posterior condyle and a thicker lateral posterior condyle, resulting in an elevation of the posterior medial femur joint line with the knee in flexion. The present invention also has a concave proximal anterior region.

Arthroplasty is the making of an artificial joint. In total knee arthroplasty there is a difficulty in reproducing the exact anatomy. The tibia is usually cut at ninety degrees (90°) to its axis in the frontal plane but the tibial plateau is at about eighty seven degree (87°). The disparity is due to the difficulty in accurately reproducing an eighty seven degrees (87°) cut. Also, it has been documented that with an eighty seven degrees (87°) or varus cut the tibial component has a tendency to loosen. (Proceedings of the Knee Society 1985–1986, Laskin, Varus Knee deformity). (Surgery of the Knee, Insall et al, 1993).

With a ninety degree (90°) cut, more bone is removed on the lateral side than on the medial side of the tibia. Neutral is defined as, parallel to a line tangent to the intact (not worn) posterior femoral condyles. When neutral femoral cuts are performed, and implants with equal medial and lateral thicknesses are used, there is a laxity of the lateral collateral ligament at ninety degrees (90°) of flexion. The lateral collateral ligament is lax in flexion because the resection of the tibia and the posterior resection of the femur are not parallel, but the prosthesis implanted has equal medial and lateral thicknesses on the tibial component and posterior condyles of the femoral component. This results in less space on the medial side and more space on the lateral side, which causes unbalanced ligaments.

The current solution to this problem is to rotate the cutting block so that more bone is removed from the posterior medial femoral condyle, this is referred to as external rotation. By externally rotating (clockwise rotation for a left knee when viewed from the distal end), the posterior femoral resection is parallel to the ninety degree (90°) tibial cut. This results in the collateral ligaments being balanced in extension and flexion when the prosthesis is implanted. The current industry standard is three degrees (3°) of external rotation which corresponds to the three degree (3°) difference between the eighty seven degree (87°) anatomical angle of the tibial plateau and the ninety degree (90°) angle of the tibial resection.

The benefits of this surgical procedure have been mentioned but there are some drawbacks. The femoral component is no longer aligned with the tibial component in full extension. The femoral component is rotated about three degrees (3°) with respect to the tibia when it is aligned parallel to the lateral plane. This malalignment potentially could cause increased wear of the tibial insert. A possible solution to this malalignment could be to externally rotate the tibial component, but this would result in reduced tibial coverage, which is not desired. Another possible solution may be to design the insert at an angle, but both turning the tibial tray externally or designing it into the insert have the problem of malalignment in flexion. With externally rotating the femoral component, there will be malalignment with the tibial insert either in flexion or extension whether the tibial tray or tibial insert is aligned straight or externally rotated.

A second problem with traditional external rotation is the chance of notching the lateral anterior femoral cortex. "Notching" occurs when more bone is removed anterolaterally than with the neutral resections resulting in a notch being created in the anterior cortex of the femur. Notching greatly increases the chances of the femur fracturing. A related problem to this is poor anteromedial implant coverage or even a gap between the implant and bone. In order to reduce the chances of notching anteriorly, the lateral side is placed flush with the cortex and a gap develops between the implant and bone anteromedially.

Another problem with traditional external rotation is the increased complexity and difficulty in instrumentation. The alignment of the cutting blocks must be variable and there is a different setup for left and right knees. Also, it can be difficult to accurately judge three degrees (3°) of external rotation when performing the surgery.

Currently there are both symmetric and asymmetric femoral components available. The symmetric components all have a patella femoral groove that is located along the centerline of the component. The asymmetric components typically have a patella femoral groove which is angled but still straight. The GENESIS knee, available from Smith & Nephew Richards Inc. is an example of this type of asymmetric femoral design. The problem with femoral components which have either design is that the patella tends to sublux laterally or to the pull toward the lateral side. This is because the patella groove is located on the centerline of the component and this is a medial to where the anatomical patella groove is located. Even with an angled patella grroove toward the lateral side the patella does not get to track a far lateral as it does normally. Most traditional femoral components have a thicker lateral anterior flange. This causes tension in the lateral retinacular which pulls the patella lateral. The current surgical solution is a soft tissue release to allow the patella to track properly.

With external rotation, the patella tracking is altered. By rotating the component as described, the lateral anterior flange is lowered and the patella groove is shifted laterally. This helps in reducing the tension in the lateral retinacular and to help locate the patella groove in a more anatomical lateral position. From zero degrees (0°) to ninety degrees (90°) of flexion benefits have been found because of lateralizing the patella in this flexion range. However, after ninety degrees (90°) of flexion, the patella will be medialized which can increase the lateral force and shear force on the patella. This can lead to higher stresses at the bone implant interface and lead to more wear of the patella implant on the patella.

Current femoral prosthesis have convex proximal anterior regions from a lateral view. This results in the patella and/or ligaments being displaced anteriorly. By having a concave anterior region, the patella and the ligaments are displaced anteriorly less because there is less metal in the concave region. This more closely resembles the anatomical femur and helps to improve patella tracking.

The objectives of the present invention are to balance the flexion and extension space, maintain proper alignment with the tibia, and to not notch the anterior femoral cortex when a ninety degree (90°) tibial resection and symmetric thickness tibial component is used. A further object of the present invention is to provide an improved femoral prosthesis which allows proper patella tracking during a normal range of knee movement.

The present invention provides an improved asymmetric femoral prosthesis for use in total knee arthroplasty and an improved method of implanting a femoral prosthesis on a patient's distal femur.

According to the invention, a knee prosthesis comprises a femoral component having an anterior articulating surface and distal and posterior articulating surface portions comprising lateral and medial condylar surfaces and an internal non-articulating surface; and a tibial component having concave articulating surfaces that receive the articulating surfaces of the femoral component during use; wherein the distance between the internal non-articulating surface and the articulating surface of the lateral condylar portion is different from the distance between the internal non-articulating surface and the articulating surface of the medial condylar portion of the femoral component over at least a part of the articulating surface of the femoral component, whereby the angle of femoral rotation about the mechanical axis changes when going through a normal range of motion of the knee.

The preferred embodiment includes a femoral prosthesis having anterior, distal, and posterior articulating surface portions. The posterior articulating surface portions include a pair of condylar surfaces that are positioned at differing distances from the anterior non-articulating or internal surface portion. The posterolateral articular surface is a greater distance from the anterior non-articulating surface than the posteromedial side. The medial and lateral articular surfaces in the distal region are the same distance from a line transverse to the component.

The femoral prosthesis has an internal non-articulating surface that includes a plurality of surfaces for receiving a resected distal femur. Preferably, the non-articulating surface includes distal, anterior and posterior surfaces as well as a pair of chamfer surfaces. Additional cut surfaces may be provided. The posterior non-articulating surface preferably defines a single plane that registers against a similarly configured resected surface of the distal femur.

The tibial component includes concave articulating surfaces that receive the femoral component articulating surfaces during use.

The improved femoral prosthesis of the present invention solves the above discussed problems that have attended traditional femoral components aligned in neutral or external rotation.

The femoral prosthesis of the present invention aligns properly with the tibia in extension because it is not rotated like the externally rotated component. This results in improved femorotibial articulation and reduces the chance of severe wear. Since the tibial component is not externally rotated there is also not rotational incongruity between the femoral and tibial components in flexion.

The angle of femoral rotation generally about the mechanical axis gradually changes when going through a normal range of motion while maintaining alignment of the femoral and tibial articular surfaces. A gradual change is defined as a change that does not produce a step or immediate shift in the articular geometry. A normal range of motion that a patient would use could range from negative ten degrees (−10°) to one hundred thirty degrees (130°). During walking on a level surface a person would typically range from 0 degrees to 70 degrees. The entire movement associated with walking is referred to as gait. The range of motion required for going up stairs is about 0 to 60 degrees and to go down stairs is about 0 to 90 degrees. Getting up out of a chair can range from 0 to 90 degrees and deep knee bending could range from 0 to 130 degrees. Hyperextension, or a negative flexion could occur while standing of about 10 degrees.

The anterolateral cortex should not be notched because no additional bone is removed. Neutral cuts are used which do not notch the anterior femur. There is improved anterior medial bone coverage because the prosthesis is not rotated (there is no gap on the anteromedial side).

The instruments for putting in the new femoral component are simpler to use because the same procedure is used for a right or left knee and the work of positioning the three degree (3°) resection is eliminated.

An alternative prosthesis and method according to the invention uses a ninety degree (90°) tibial resection and a tibial component that is thicker on the lateral side than the medial side. The femoral component then preferably provides a thinner lateral distal condyle than the medial distal condyle. The posterior condyles are preferably of equal thickness at about ninety degrees (90°) of flexion in this embodiment.

With the present invention the thickness could be altered both distally and posteriorly, simply by making an angled distal resection in the frontal plane or making an angled posterior resection with respect to neutral rotation. If the anterior resection was made neutral and the posterior resection was rotated then the cross section from anterior to posterior would be trapezoidal in shape.

Differences between the positions of the medial and lateral articular surfaces are independent of the box geometry and any variation of distal or posterior condyle thickness. The distal or posterior cuts could be made at an angle or at different levels in order to produce the same design objective but maintain constant condyle thicknesses or to maintain different condyle thicknesses. This would produce the same results of balancing the flexion and extension spaces, with proper alignment with the tibia, and have different thicknesses than in the description of this new femoral prosthesis.

The femoral component could also be designed with more or less external rotation incorporated. With traditional neutral resections of the distal and posterior femur, in order to design for more external rotation there would be a larger difference in the thickness of the posterior condyles with the preferred embodiment. The medial posterior condyle is thinner than the lateral posterior condyle of the femoral component so that at ninety degrees (90°) of flexion the femoral joint line is angled at three (3°) of rotation along its mechanical axis. Other angles could be designed into the femoral ranging from about one degree (1°) to ten degrees (10°) at about ninety degrees (90°) of flexion. The articular geometry of the condyles changes such that the femoral component articulates with the tibial component during flexion and extension without requiring the femoral component to turn relative to the alignment of the tibial insert in the transverse plane.

In order to solve the problem of improper patella tracking, the invention provides a knee prosthesis comprising a femoral component having internal non-articulating surfaces and external articulating surfaces, including an anterior articulating surface and distal and posterior lateral and medial condylar articulating surfaces, a centerline of the femoral component being defined centrally between the distal condyles of the component; a patella component or natural patella having an articulating surface which articulates with the anterior articulating surface of the femoral component in use, said femoral component having a patella groove in its anterior articulating surface within which said patella component may track during normal articulating motion of the knee; the longitudinal axis of said groove being located laterally with respect to said centerline in the superior region of the anterior articulating surface and curving in a medial direction in the distal region of the anterior articulating surface of the femoral component.

The patella groove has been shifted laterally to allow the patella to track in its more anatomical location. The groove is located lateral of the centerline in the anterior region and then curves back, preferably to the centerline of the component. The lateral shift of the patella groove allows the patella to track in its anatomical location and it reduces the tension on the ligaments that pull the patella laterally. The lateral shift is only limited by the width of the component.

The new asymmetric femoral component may also have a concave proximal anterior region in a lateral view. This results in the femoral component being thinner in this region. The benefits are that the thickness of the implant more closely matches the thickness of the bone that is removed. The patella and the ligaments can function more anatomically because extra metal is not being added to the anterior cortex of the femur. The concave region has an arc center that is located anterior to the component where a convex region would have an arc center that is posterior to the anterior surface of the component.

The present invention also provides an improved method of implanting a femoral prosthesis on a patient's distal femur. The distal femur is first resected with a plurality of five cuts including anterior, posterior, distal and a pair of chamfer cuts. The femoral prosthesis is affixed to the patient's resected distal femur. The femoral prosthesis is an improved asymmetric prosthesis having anterior, posterior, and distal non-articulating portions that closely fit the anterior, posterior and distal cuts on the distal femur.

The patient's tibia is resected to receive a tibial prosthesis. The femoral and tibial cuts are generally parallel in full extension and relative to the tibial prosthesis and to the femoral prosthesis so that the angle of femur rotation generally about the patient's mechanical axis relative to the tibia gradually changes when going through a normal range of motion of the patient's knee from about minus twenty degrees (i.e. −20°) of flexion to about one hundred thirty degrees (130°) of flexion while maintaining alignment of the femoral and tibial articular surfaces.

The femoral posterior resections are made parallel to a line tangent to the intact posterior femoral condyles with approximately the same amount of bone being removed off of each posterior condyle, but the prosthesis has a thinner medial posterior condyle than its lateral posterior condyle. The distal thickness is the same between the medial and lateral condyles in the preferred embodiment. This results in balancing both the flexion and extension spaces similar to that of externally rotating a traditional femoral prosthesis.

For a further understanding of the nature and objects of the present invention, reference should be had to the following detailed description, which is given only as an example of the present invention, taken in conjunction with the accompanying drawings, in which like parts are given like reference numerals, and wherein.

Figure 1:
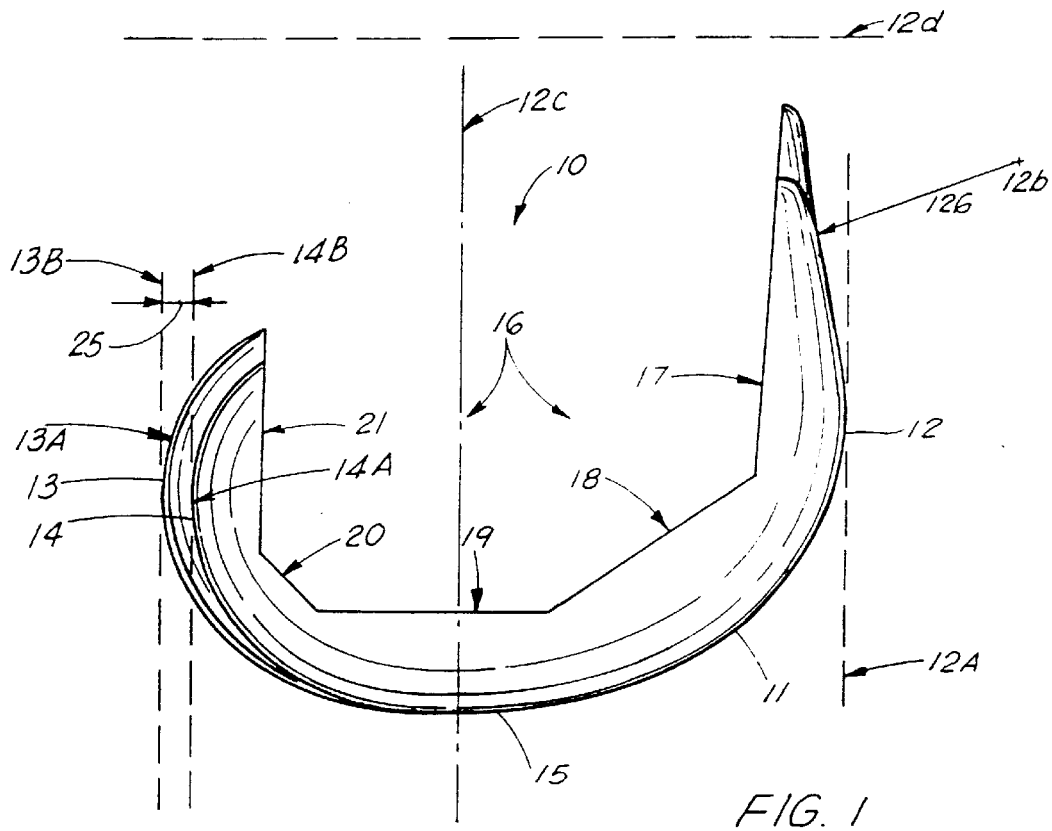
FIG. 1 is a lateral view of the preferred embodiment of the present invention showing the medial and lateral posterior condyle thickness and the concave anterior region.
Figure 2:
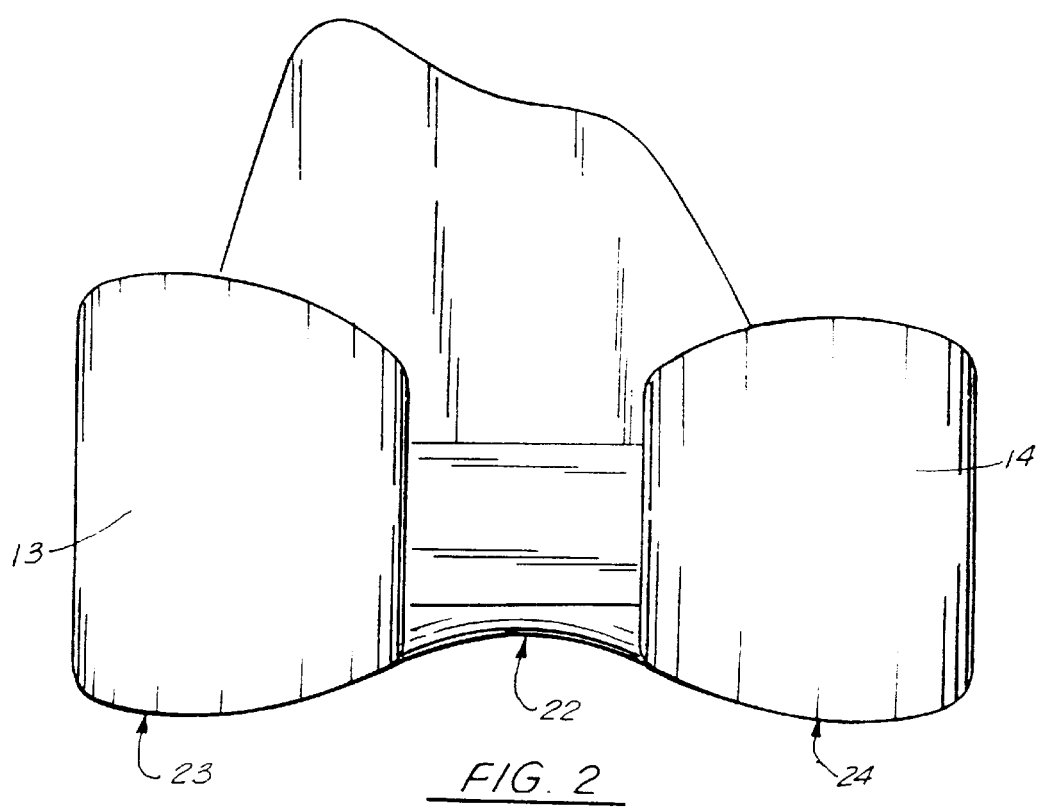
FIG. 2 is a frontal view of the preferred embodiment of the apparatus of the present invention.

FIGS. 1 and 2 show generally the preferred embodiment of the apparatus of the present invention designated generally by the numeral 10. The asymmetric femoral component 10 includes a prosthesis articulating surface 11 that includes an anterior articulating surface portion 12, distal articulating surface 15, and a pair of condylar surfaces including lateral posterior condyle 13 having posterior condylar surface 13A and medial posterior surface condyle 14 having posterior condylar surface 14A.

The proximal side of asymmetric femoral prosthesis 10 provides a recess 16 that receives a patient's distal femur after the distal femur has been resected to fit the plurality of surfaces 17–21. Anterior proximal surface 17 is a generally flat surface that intersects proximal anterior chamfer 18. Anterior chamfer 18 extends between anterior proximal surface 17 and proximal surface 19. Proximal posterior chamfer 20 extends between surface 19 and posterior proximal surface 21. In FIG. 2, asymmetric femoral prosthesis 10 has a central recess portion 22 between lateral distal surface 23 and medial distal surface 24.

In FIG. 1, there can be seen a difference in the position between the surfaces 13A–14A. A line drawn tangent to the most posterior portion of lateral posterior condyle 13, generally parallel to the frontal plane, is defined by the line 13B. A line drawn tangent to the most posterior point on posterior condylar surface 14A (generally parallel to frontal plane) is the line 14B. A distance 25 between the lines 13B and 14B shows that the lateral posterior condyle 13 is thicker than the medial posterior condyle 14 whereas the inner surface 21 of each of the condyles 13 and 14 is the same flat surface 21, defining a plane that accepts corresponding resected surfaces on the patient's distal femur. The frontal plane or coronal plane is shown in FIG. 1 as a plane going through line 12C and perpendicular to the page. It is a plane that splits the body into a front and a rear half. The transverse plane is typically a plane that goes through the waist area and cuts the body into a top and a bottom half. For ease of use it is shown in FIG. 1 as a plane going through line 12d and perpendicular to the page. This plane is parallel to the typical transverse plane and for this description is functionally the same.

This femoral component 10 essentially has three degrees (3°) of external rotation built into it. This is in contrast to the current procedure of the surgeon cutting the femur at three degrees (3°) of external rotation. On the femoral component 10 of the present invention, the angle of femoral rotation generally about the mechanical axis 32 gradually changes when going through a normal range of motion of the patient's knee, typically from about zero degrees (0°) of flexion to about ninety (90°) to one hundred thirty degrees (130°) of flexion. A normal range of motion that a patient would use could range from negative ten degrees (–10°) to one hundred thirty (130°) degrees. During walking on a level surface a person would typically range from 0 degrees to 70 degrees. The entire movement associated with walking is referred to as gait. The range of motion required for going up stairs is about 0 to 60 degrees and to go down stairs is about 0 to 90 degrees. Getting up out of a chair can range from 0 to 90 degrees and deep knee bending could range from 0 to 130 degrees. Hyperextension, or a negative flexion could occur while standing of about 10 degrees. The rotation balances the flexion gap between the femoral and tibial components as well as aligning the femoral component articular surface parallel to the lateral plane in flexion and extension. The three degrees (3°) of external rotation is generally along the mechanical axis 32 of the femur.

Figure 4:
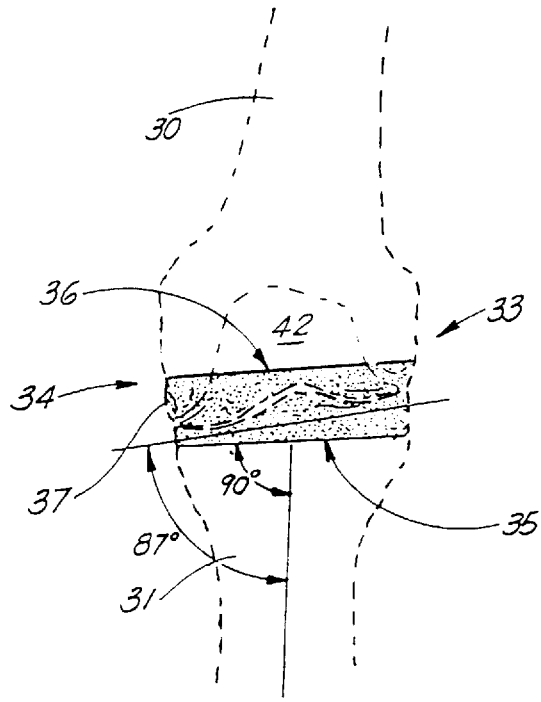
FIG. 4 is a frontal view of a human knee joint showing a ninety degree (90°) tibia resection and a parallel femoral distal resection.
Figure 5:
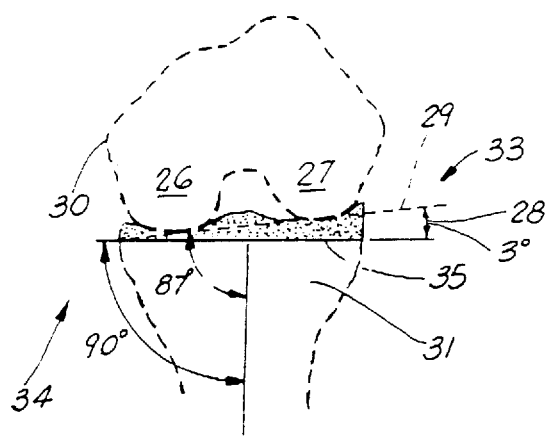
FIG. 5 is a frontal view of a human knee joint in ninety degree (90°) flexion illustrating the anatomical angle of the tibia at eighty seven degree (87°) and the tibial resection at ninety degrees (90°)

In total knee arthroplasty there is a difficulty in reproducing the exact anatomy. As illustrated in FIGS. 4 and 5, the patient's tibia 31 is usually cut at ninety degrees (90°) to its axis in the frontal plane but the tibial plateau is at eighty seven degrees (87°). The disparity is due to the difficulty in accurately reproducing an eighty seven degree (87°) cut. Also, it has been documented that with an eighty seven degree (87°) or varus cut the tibial component has a tendency to loosen. (Proceedings of the Knee Society 1985–1986, Laskin, Varus Knee deformities).

Figure 3:
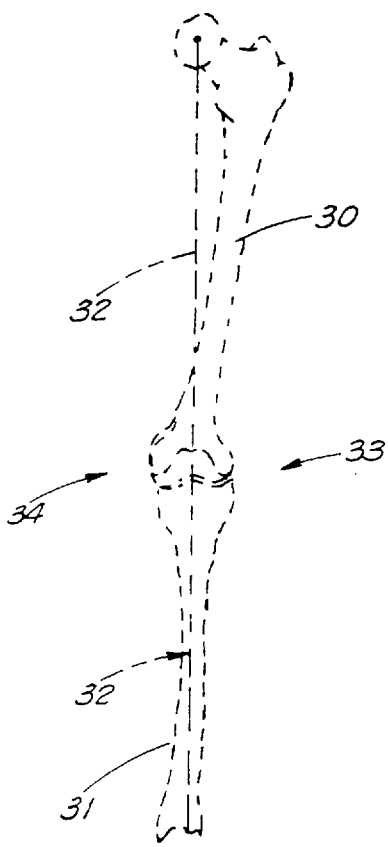
FIG. 3 is a frontal view illustrating human femur, knee joint, and tibia and the leg mechanical axis.
Figure 7:
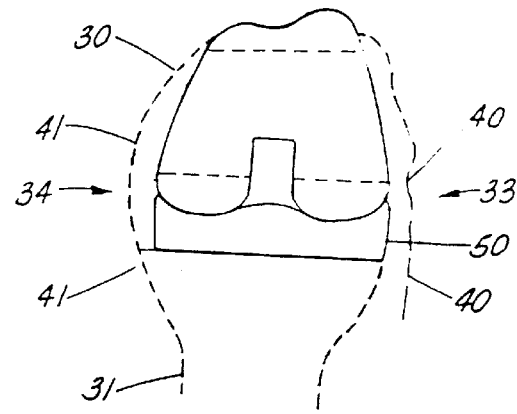
FIG. 7 is a frontal view of a human knee joint in ninety degrees (90°) of flexion showing a symmetric thickness tibial and femoral prosthesis in neutral alignment.

With a ninety degree (90°) cut, more bone is removed on the lateral side 33 than on the medial side 34 of the tibia 31 as shown in FIGS. 3, 4, and 5. In FIG. 4, the tibial cut is designated as 35. Because of this, at ninety degrees (90°) of flexion, when neutral femoral cuts are performed the resection 35 of the tibia and the posterior resections 38 and 39 of the femur are not parallel. This results in less space on the medial side 34 and more space on the lateral side 33, which causes unbalanced ligaments 40 and 41 when traditional tibial and femoral components are used that have symmetric thicknesses on the medial and lateral sides (see FIG. 7).

Figure 8:
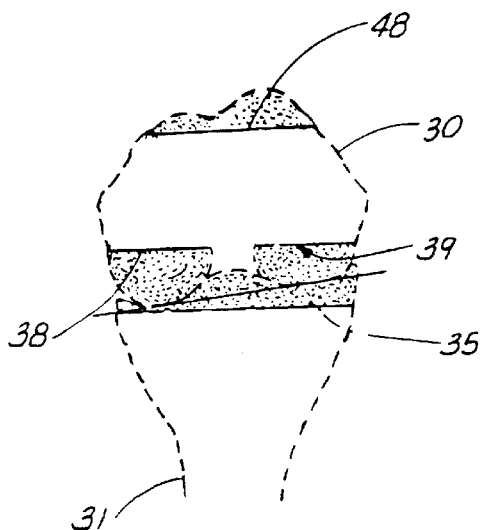
FIG. 8 is a frontal view of a human knee joint illustrating externally rotated resections on the anterior and posterior femur and showing more bone cut from the anterolateral femur and from the posteromedial femur.
Figure 9:
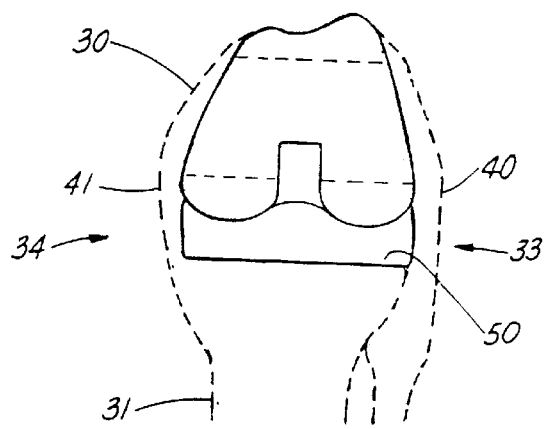
FIG. 9 is a frontal view of a knee joint in ninety degrees (90°) of flexion with a symmetric thickness tibial and femoral prosthesis externally rotated and the balanced collateral ligaments.

The current solution to this problem is to rotate the cutting block so that more bone is removed from the posteromedial femoral condyle. This is referred to in the art as external rotation. By externally rotating (clockwise rotation for a left knee when viewed from the distal end), the posterior femoral resection is parallel to the ninety degree (90°) tibial cut (see FIG. 8). This results in the collateral ligaments 40 and 41 being balanced in extension and flexion when the prosthesis is implanted as shown in FIG. 9. The current industry standard is three degrees (3°) of external rotation.

Figure 6:
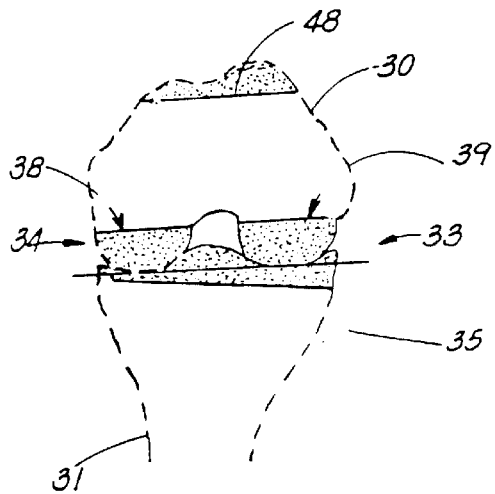
FIG. 6 is a frontal view of a human knee joint in ninety degrees (90°) of flexion illustrating neutral femoral posterior and anterior resections with a ninety degree (90°) tibial resection.
Figure 10:
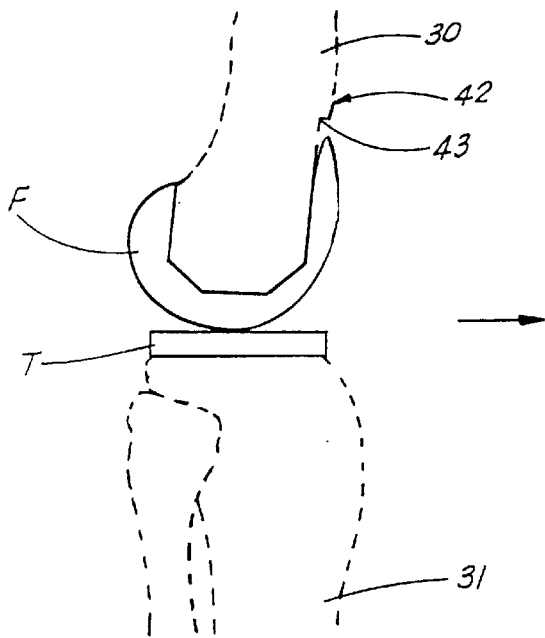
FIG. 10 is a lateral view illustrating a femur that has been notched in the anterior cortex as part of a prior art knee joint replacement surgical procedure.

One problem with traditional external rotation is the chance of notching the anterolateral femoral cortex as illustrated in FIG. 10 with prior art femoral prosthesis F and tibial prosthesis T. FIG. 8 shows that more bone is removed anterolateral and posteromedial than with the femoral neutral resections shown in FIG. 6. FIG. 10 illustrates the anterior cortex 42 with a notch 43, which greatly increases the chance of the femur fracturing.

Figure 11:
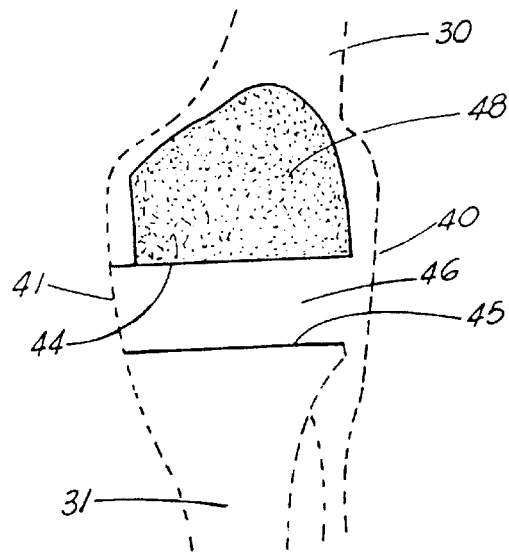
FIG. 11 illustrates knee joint resections using the method of the present invention and showing the extension space parallel.
Figure 12:
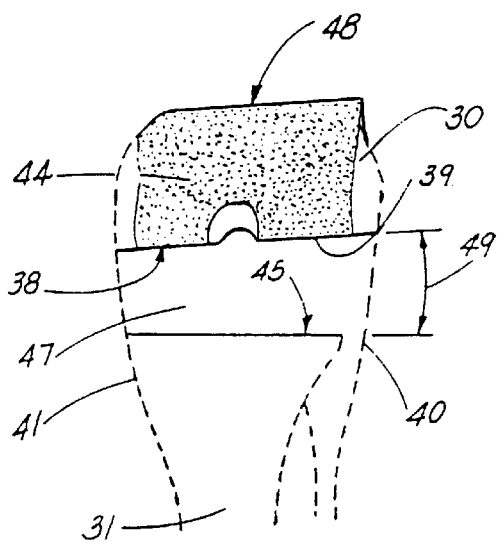
FIG. 12 illustrates the neutral femoral resections using the method of the present invention, showing the flexion space that is trapezoidally shaped.
Figure 13:
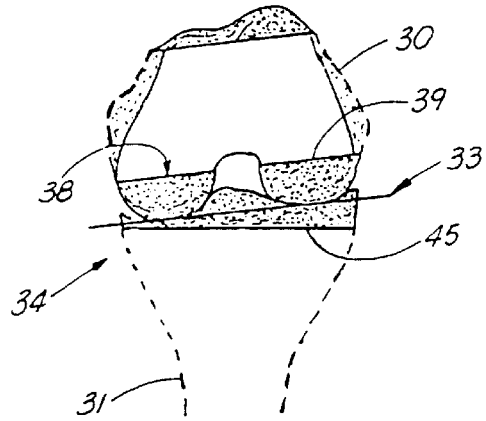
FIG. 13 is a frontal view of a knee joint in ninety degrees (90°) of flexion showing neutral femoral resections of the anterior cortex and posterior condyles.
Figure 14:
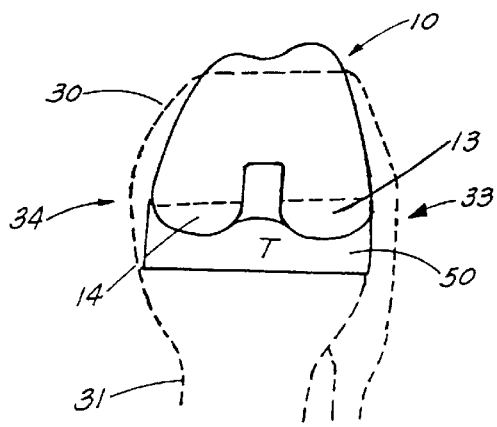
FIG. 14 is a frontal view of the preferred embodiment of the present invention of a knee joint ninety degrees (90°) in flexion showing a thinner posteromedial condyle than the posterolateral and balanced collateral ligaments.
Figure 15:
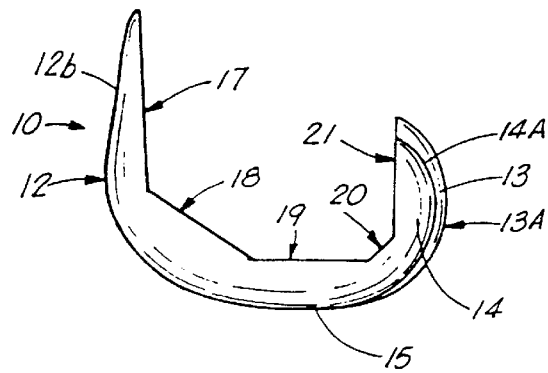
FIG. 15 is a lateral view of the preferred embodiment of the asymmetric component of the present invention showing the different medial and lateral curves posteriorly.

In the preferred embodiment, the femoral posterior resections are made neutral with approximately the same amount of bone being removed off of each posterior condyle, but the prosthesis has a thinner medial posterior condyle 14 than its lateral posterior condyle 13 as seen in FIG. 14. The distal thickness is the same between the medial and lateral condyles in the preferred embodiment as shown in FIG. 15. This results in balancing both the flexion and extension spaces similar to that of externally rotating a traditional femoral prosthesis. FIGS. 11 and 12 show neutral femoral resections as used in the method of the present invention. The distal femoral resection is indicated as 44, the tibial resection as 45, defining a parallel extension space 46. The anterior resection is indicated as 48 in FIGS. 11 and 12. In FIG. 12, posterior femoral resections 38 and 39 appear when the knee is in flexion, defining a trapezoidal flexion space 47.

Figure 16:
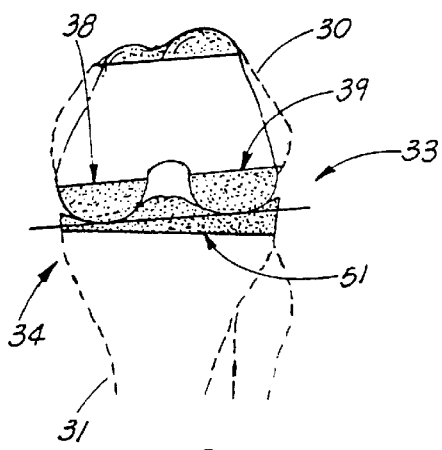
FIG. 16 is a frontal view of a knee in ninety degree (90°) of flexion of an alternate embodiment of the method and apparatus of the present invention showing neutral femoral resections.
Figure 17:
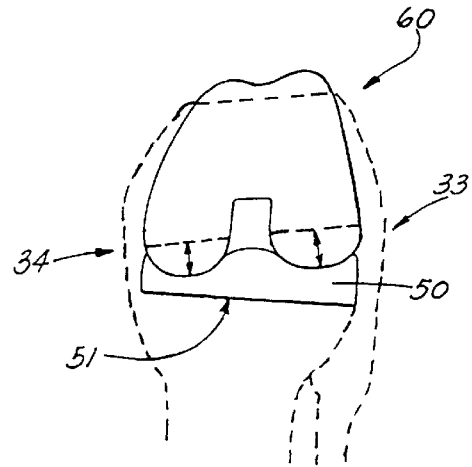
FIG. 17 is a frontal view of a knee joint in ninety degrees (90°) of flexion showing the alternate embodiment of the apparatus of the present invention with a tibial component that has a thicker lateral section that it's medial section.
Figure 18:
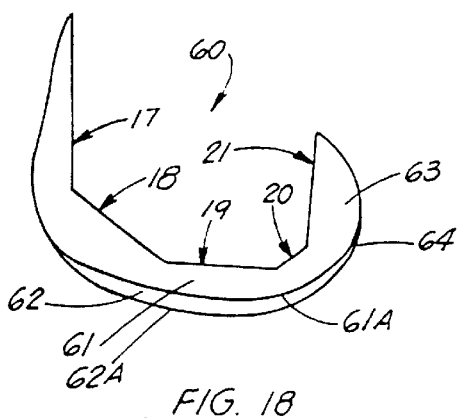
FIG. 18 is a lateral view of the alternate embodiment of the asymmetric femoral component of the present invention showing the different medial and lateral curves distally.

An alternative method and apparatus is shown in FIGS. 16–18. The alternate embodiment of the method and apparatus of the present invention uses a ninety degree (90°) tibial resection 51 and a tibial component 50 that is thicker on the lateral side than the medial side. The femoral component 60 would then have a thinner lateral distal condyle 61 than the medial distal condyle 62. The posterior condyles 63 and 64 would then have the same thickness at about ninety degrees (90°) of flexion in the alternate embodiment.

With the present invention the thickness could be altered both distally and posteriorly simply by making an angled distal resection in the frontal plane or making an angled posterior resection with respect to neutral rotation. If the anterior resection was made neutral and the posterior resection was angled then the cross section from anterior to posterior would be trapezoidal in shape in the transverse plane.

The asymmetric femoral prosthesis components 10 and 60 shown in FIGS. 13–18 show that the difference between the medial and lateral sides is independent of the box geometry and any variation of distal or posterior condyle thickness. The distal or posterior cuts could be made at an angle or at different levels in order to produce the same design objective but maintain constant condyle thicknesses or to maintain different condyle thicknesses. This would produce the same results of balancing the flexion and extension spaces, with proper alignment with the tibia, and have different thicknesses in the condyles than in the description of this new femoral prosthesis.

The femoral component could also be designed with more or less external rotation built in. With traditional neutral resections of the distal and posterior femur, there would be a larger difference in the thickness of the posterior prosthesis condyles to produce more external rotation.

The new femoral component design is intended to be placed to compensate for a ninety degree (90°) tibial resection. Resecting the tibia at ninety degrees (90°) in the frontal plane and placing a prosthetic tibial component, which has the same thickness medially and laterally, results in an elevated medial compartment of the tibia. To compensate for this, the femoral component of the present invention, in conjunction with the resections of the distal and posterior femur, elevate the medial joint line relative to the femur to compensate for the elevation that occurs in the tibia.

On the posterior femur, this is accomplished by resecting the posterior femur roughly parallel to the posterior femoral condyle joint line. The prosthetic medial femoral condyle is thinner than the resection that occurs medially. This results in an elevation of the posterior medial femoral joint line with the knee in flexion.

The distal resection of the femur is accomplished by removing asymmetrical amounts of bone from the medial and lateral condyles of the femur. The distal medial and lateral surfaces are then replaced with equal thicknesses of prosthetic medial and lateral surfaces. Because additional bone has been removed from the medial distal femoral condyle, this results in an elevation of the medial distal femoral joint line with the knee in extension. This too compensates for elevation of the medial compartment of the tibial that occurs due to the ninety degree (90°) tibial resection in the frontal plane.

Figure 19:
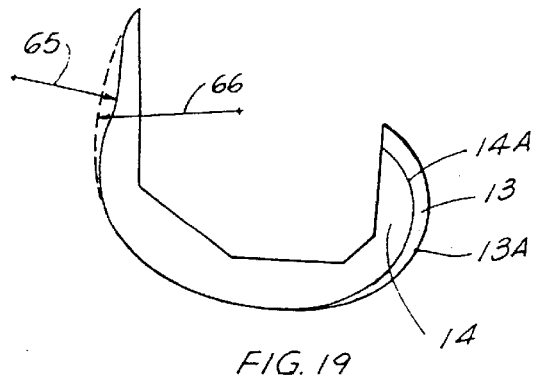
FIG. 19 is a lateral view of a femoral component showing both the traditional convex anterior and the concave anterior region.

FIG. 19 shows a lateral view of a femoral component. The anterior region 65 shows the concave region of the new femoral where the arc center is located anterior to the component. The anterior region 66 shows the convex region of a traditional femoral component where the arc center is located posterior to the anterior surface. The concave anterior results in less metal anteriorly as shown in FIG. 19 which more closely replaces the resected bone with the same amount of metal.

Figure 20:
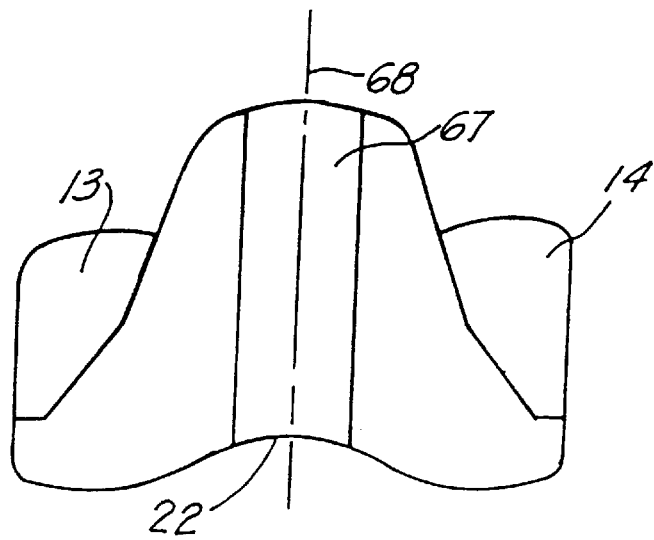
FIG. 20 is a frontal view of a prior art femoral component showing a centrally located patella groove.
Figure 21:
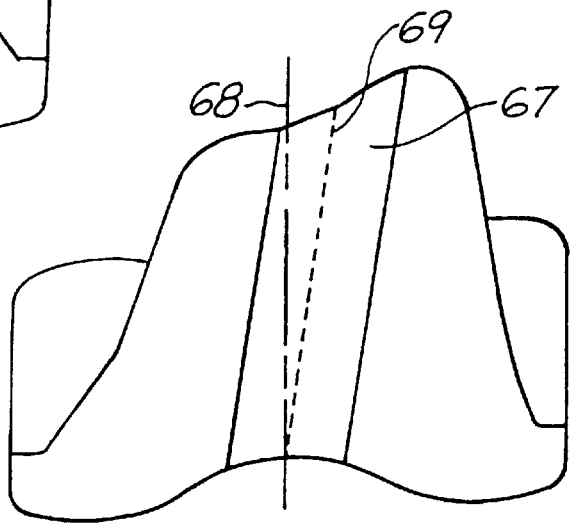
FIG. 21 is a frontal view of a prior art femoral component showing an angled patella groove.

FIGS. 20 and 21 show prior art prostheses in which the patella groove 67 is either centrally positioned with respect to the centerline 68 of the femoral component (FIG. 20) or is angled (FIG. 21).

Figure 22:
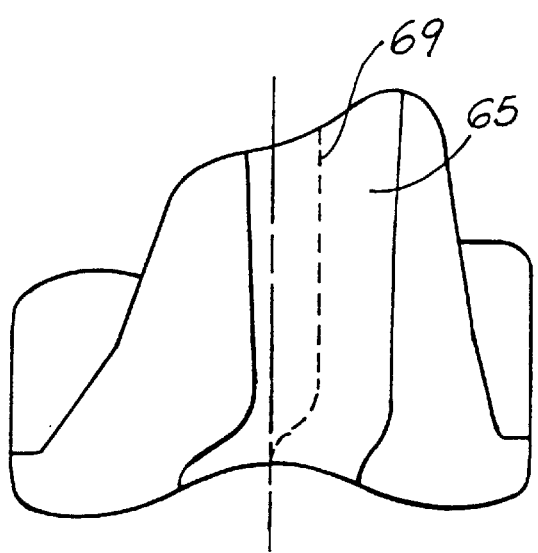
FIG. 22 is a frontal view of an improved femoral component of the invention.
Figure 23:
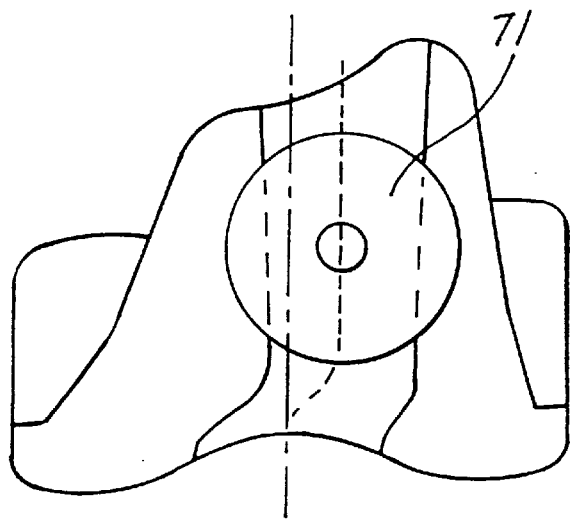
FIG. 23 is a similar view showing the position of the patella
Figure 24:
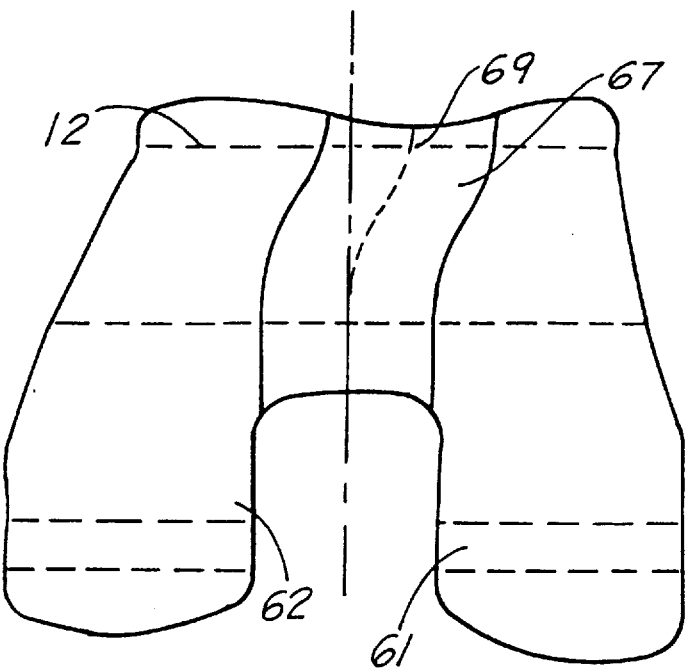
FIG. 24 is a distal view of the improved femoral component showing the location of the patella groove.
Figure 25:
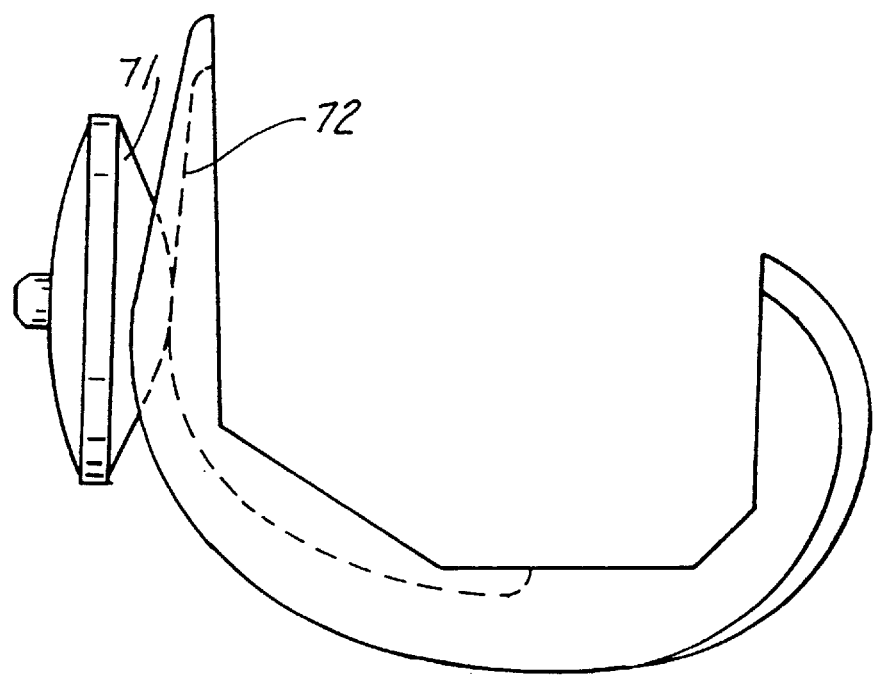
FIG. 25 is a medial view of an improved femoral component showing the patella groove.

By contrast, the improved femoral component of FIG. 22 has a patella groove which is positioned lateral of and about parallel to centerline 68 in the anterior region 65 of the component and then curves back to the centreline 68 at the intracondylar notch 70. The depth of the groove 67 is shown in FIG. 25 by line 72. By lateralizing the patella femoral groove, the ligaments are more balanced and the patella potentially tracks smoother and properly in the patella femoral groove. The new design is a patella femoral groove which is aligned virtually straight in the anterior region but shifted lateral to the centerline and which gradually transitions into the intracondylar notch region. This type of patellofemoral groove design causes the patella to track much more lateral at higher degrees of flexion than compared to a centerline or angled patella femoral groove design. This has a clinical advantage because it allows the patella to track properly which should avoid the need for soft tissue lateral releases. The patella is allowed to track laterally up to about 40 to 50 degrees of flexion before it gradually transitions to the centerline of the component in the intracondylar notch as shown in FIG. 24. It transitions into the intracondylar notch so that there is good contact between the femoral component and the patella at high degrees of flexion.

The following table lists the parts numbers and parts descriptions as used herein and in the drawings attached hereto.

PARTS LIST

| Part Number | Description |
| --- | --- |
| 10 | asymmetrical femoral prosthesis |
| 11 | prosthesis articulating surface |
| 12 | anterior articulating surface |
| 12A | anterior tangent line |
| 12B | anterior concave surface |
| 12C | frontal plane |
| 12D | transverse plane |
| 13 | lateral posterior condyle |
| 13A | posterior condylar surface |
| 13B | posterolateral tangent line |
| 14 | medial posterior condyle |
| 14A | posterior condylar surface |
| 14B | posteromedial tangent line |
| 15 | distal surface |
| 16 | proximal recess |
| 17 | anterior proximal surface |
| 18 | proximal anterior chamfer |
| 19 | proximal surface |
| 20 | proximal posterior chamfer |
| 21 | posterior proximal surface |
| 22 | recess |
| 23 | lateral distal surface |
| 24 | medial distal surface |
| 25 | offset distance |
| 26 | medial distal surface |
| 27 | lateral distal surface |
| 28 | angle |
| 29 | anatomical angle tibia |
| 30 | femur |
| 31 | tibia |
| 32 | mechanical axis |
| 33 | lateral side |
| 34 | medial side |
| 35 | ninety degree tibial resection |
| 36 | distal femoral resection |
| 37 | extension space |
| 38 | femoral resection - posteromedial |
| 39 | femoral resection - posterolateral |
| 40 | lateral collateral ligament |
| 41 | medial collateral ligament |
| 42 | anterior femoral cortex |
| 43 | notch |
| 44 | distal femoral resection |
| 45 | ninety degree tibial resection |
| 46 | extension space - parallel |
| 47 | flexion space - trapezoidal |
| 48 | anterior resection |
| 49 | angle |
| 50 | tibial component |
| 51 | tibial resection |
| F | femoral prosthesis |
| T | tibial prosthesis |
| 60 | femoral component |
| 61 | lateral distal condyle |
| 61A | lateral distal surface |
| 62 | medial distal condyle |
| 62A | medial distal surface |
| 63 | posterolateral condyle |

-continued

| Part Number | Description |
| --- | --- |
| 64 | posteromedial condyle |
| 65 | concave anterior region of new asymmetric femoral |
| 66 | convex anterior region of traditional femoral |
| 67 | patella groove |
| 68 | centerline of the femoral component |
| 69 | longitudinal axis of patella groove |
| 70 | intracondylar notch |
| 71 | patella component |
| 72 | line showing depth of patella groove |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

We claim:

1. A knee prosthesis for surgical implantation in a patient's knee having a mechanical axis and a normal range of motion comprising:
   a) a femoral component having distal and posterior articulating surface portions comprising lateral and medial condylar articulating surfaces and an internal non-articulating surface;
   b) a tibial component having concave articulating surfaces that receive the articulating surfaces of the femoral component during use,
   c) wherein the distance between the internal non-articulating surface and the lateral condylar articulating surface is different from the distance between the internal non-articulating surface and the medial condylar articulating surface of the femoral component and
   d) wherein the different distance so measures over a sufficient area of the articulating surfaces to enable the angle of femoral rotation about the mechanical axis changes when going through a normal range of motion of the knee.

2. A knee prosthesis as claimed in claim 1 wherein the patient's femur has a frontal plane and the posterior articulating surface portions include posterior lateral and medial condylar surface portions positioned at differing distances from the frontal plane of the patient's femur, and wherein the lateral condylar surface portion is spaced farther from said frontal plane than the medial condylar surface portion.

3. A knee prosthesis as claimed in claim 2 wherein the femoral component comprises medial and lateral posterior condylar portions that have different thicknesses measured respectively from the posterior non-articulating surface to the posterior articulating surface at the respective posterior condylar portions.

4. A knee prosthesis as claimed in claim 1, wherein the distal medial condylar surface portion is spaced farther from a transverse plane than is the distal lateral condylar surface and the thickness of the posterior lateral and medial condylar portions is the same; and
   where during use, the angle of femoral rotation about the mechanical axis changes when going through a normal range of motion of the patient's knee.

5. A knee prosthesis as claimed in claim 4, wherein said tibial component has medial and lateral sides and is thicker on the lateral side than on the medial side.

6. The knee prosthesis of claim 1 wherein the non-articulating surface comprises a plurality of intersecting surfaces including at least distal and posterior surfaces.

7. The knee prosthesis of claim 6 wherein the posterior non-articulating surface defines a single plane.

8. The knee prosthesis of claim 6 wherein the posterior non-articulating surface is substantially flat and forms an angle of at least ninety degrees with the distal non-articulating surface.

9. The knee prosthesis of claim 1 wherein the non-articulating surfaces comprises flat intersecting planes.

10. The knee prosthesis of claim 1 further comprising an anterior articulating surface.

11. The knee prosthesis of claim 10 further comprising an anterior non-articulating surface, and wherein the anterior non-articulating surface is substantially flat and forms an angle of at least ninety degrees with the distal non-articulating surface.

12. The knee prosthesis of claim 1 wherein the angle of femoral rotation about the mechanical axis gradually changes when going through a range of motion from zero degrees of flexion to about ninety degrees (90°) of flexion.

13. The knee prosthesis of claim 1 wherein the angle of femoral rotation about the mechanical axis gradually changes when going through a range of motion from zero degrees of flexion to about one hundred thirty degrees (130°) of flexion.

14. The knee prosthesis of claim 1 wherein the angle of femoral rotation about the mechanical axis gradually changes when going through a range of motion from about negative twenty degrees (−20°) of flexion to about ninety degrees (90°) of flexion.

15. The knee prosthesis of claim 1 wherein the angle of femoral rotation about the mechanical axis gradually changes when going through a range of motion from about negative twenty degrees (−20°) of flexion to about one hundred forty degrees (140°) of flexion.

16. The knee prosthesis of claim 1 wherein the angle of femoral rotation about the mechanical axis gradually changes when going through a range of motion from about twenty degrees (20°) of flexion to about eighty degrees (80°) of flexion.

17. The knee prosthesis of claim 1 wherein the angle of femoral rotation about the mechanical axis gradually changes when going through a range of motion of about sixty degrees (60°).

18. The knee prosthesis of claim 1 wherein the angle of femoral rotation about the mechanical axis gradually changes when going through a range of motion of about eighty degrees (80°).

19. The knee prosthesis of claim 1 wherein the angle of femoral rotation about the mechanical axis gradually changes when going through a range of motion of about ninety degrees (90°).

20. A knee prosthesis as claimed in claim 1 wherein said femoral component further comprises a patella groove located in the anterior articulating surface for articulation with a patella or patella component, said groove having a longitudinal axis which is located laterally of a longitudinal centerline of the component in the superior region of the anterior articulating surface and curves towards a medial direction in the distal region of the femoral component.

21. A knee prosthesis as claimed in claim 20 wherein the axis of said groove is substantially parallel to said centreline in the superior region of the anterior articulating surface.

22. A knee prosthesis as claimed in claim 20 wherein the axis of said groove is located substantially at the centerline in the distal region of the femoral component.

23. A knee prosthesis as claimed in either claim 20 or claim 21 or claim 22, wherein the change in the location of the longitudinal axis of said groove from lateral of the centerline towards medial is gradual.

24. A knee prosthesis as claimed in claim 20 wherein said patella groove is curved over at least a part of its length.

25. A knee prosthesis comprising:
   a) a femoral component having internal non-articulating surfaces and external articulating surfaces, including an anterior articulating surface and distal and posterior lateral and medial condylar articulating surfaces
   b) a centerline of the femoral component being defined centrally between the distal condyles of the component
   c) a patella component having an articulating surface which articulates with the anterior articulating surface of the femoral component in use
   d) said femoral component having a patella groove in its anterior articulating surface within which said patella component may track during normal articulating motion of the knee
   e) the longitudinal axis of said groove being located laterally with respect to said centerline in the superior region of the anterior articulating surface and curving in a medial direction in the distal region of the anterior articulating surface of the femoral component.

26. A knee prosthesis as claimed in claim 25 wherein the axis of said groove is substantially parallel to said centerline in the superior region of the anterior articulating surface.

27. A knee prosthesis as claimed in claim 25 wherein the axis of said groove is located substantially at the centerline in the distal region of the femoral component.

28. A knee prosthesis as claimed in either claim 25 or claim 26 or claim 27, wherein the change in the location of the longitudinal axis of said groove from lateral of the centerline towards medial is gradual.

29. A knee prosthesis as claimed in claim 25 wherein said patella groove is curved over at least a part of its length.

30. A method of implanting a femoral prosthesis on a patient's distal femur comprising the steps of:
   a) resecting the patient's distal femur with a plurality of cuts including at least posterior and distal cuts, wherein the posterior cuts remove portions of the patient's posterior condyles; and
   b) affixing a femoral prosthesis to the patient's resected distal femur, wherein the prosthesis has an internal non-articulating surface including at least posterior and distal non-articulating portions that closely fit the posterior and distal cuts made in step "a", wherein the femoral prosthesis has medial and lateral posterior condylar portions with articulating surfaces and the medial and lateral posterior condylar portions with articulating surfaces are spaced at different distances from the internal non-articulating surface such that the different distances extend over a sufficient area of the articulating surfaces to enable the angle of femoral rotation about a mechanical axis to change when going through a normal range of motion of the knee.

31. The method of claim 30 wherein the distal femur is resected with at least distal, anterior, and posterior cuts.

32. The method of claim 30 wherein in step "b" the prosthesis has medial and lateral distal condylar portions with articulating surfaces that are spaced different distances from the distal cut.

33. The method of claim 32 wherein the angle of femoral rotation about the mechanical axis gradually changes when going through a range of motion of about sixty degrees (60°).

34. The method of claim 32 wherein the angle of femoral rotation about the mechanical axis gradually changes when going through a range of motion of about eighty degrees (80°).

35. The method of claim 32 wherein the angle of femoral rotation about the mechanical axis gradually changes when going through a range of motion of about ninety degrees (90°).

36. The method of claim 30 the angle of femoral rotation about the patient's mechanical axis gradually changes when going through a range of motion from zero degrees of flexion to about ninety degrees (90°) of flexion.

37. The method of claim 30 the angle of femoral rotation about the patient's mechanical axis gradually changes when going through a range of motion from zero degrees of flexion to about one hundred thirty degrees (130°) of flexion.

38. The method of claim 30 the angle of femoral rotation about the patient's mechanical axis gradually changes when going through a range of motion from about negative twenty degrees (−20°) of flexion to about ninety degrees (90°) of flexion.

39. The method of claim 30 the angle of femoral rotation about the patient's mechanical axis gradually changes when going through a range of motion from about negative twenty degrees (−20°) of flexion to about one hundred forty degrees (140°) of flexion.

40. The method of claim 30 the angle of femoral rotation about the patient's mechanical axis gradually changes when going through a range of motion from about twenty degrees (20°) of flexion to about eighty degrees (80°) of flexion.

* * * * *